(12) United States Patent
Hastings et al.

(10) Patent No.: US 7,248,914 B2
(45) Date of Patent: Jul. 24, 2007

(54) METHOD OF NAVIGATING MEDICAL DEVICES IN THE PRESENCE OF RADIOPAQUE MATERIAL

(75) Inventors: Roger N. Hastings, Maple Grove, MN (US); Steven J. Ferry, Excelsior, MN (US); Demetrius K. Lopes, Chicago, IL (US)

(73) Assignee: Stereotaxis, Inc., St. Louis, MO (US)

( * ) Notice: Subject to any disclaimer, the term of this patent is extended or adjusted under 35 U.S.C. 154(b) by 694 days.

(21) Appl. No.: 10/186,264

(22) Filed: Jun. 28, 2002

(65) Prior Publication Data

US 2004/0002643 A1 Jan. 1, 2004

(51) Int. Cl.
*A61B 5/05* (2006.01)

(52) U.S. Cl. ............... 600/424; 606/130; 128/897; 128/899

(58) Field of Classification Search ........ 600/373, 600/407, 411, 420–424, 585; 606/1, 108, 606/130; 128/897–925
See application file for complete search history.

(56) References Cited

U.S. PATENT DOCUMENTS

| | | | |
|---|---|---|---|
| 3,358,676 A * | 12/1967 | Frei et al. .............. 600/12 |
| 4,173,228 A | 11/1979 | Van Steenwyk et al. |
| 5,211,165 A * | 5/1993 | Dumoulin et al. .......... 600/410 |
| 5,558,091 A | 9/1996 | Acker et al. |
| 5,868,674 A * | 2/1999 | Glowinski et al. .......... 600/410 |
| 6,157,853 A * | 12/2000 | Blume et al. ............... 600/426 |
| 6,165,193 A * | 12/2000 | Greene et al. .............. 606/191 |
| 6,216,030 B1 * | 4/2001 | Howard et al. ............. 600/427 |
| 6,253,770 B1 * | 7/2001 | Acker et al. ................ 128/899 |
| 6,272,370 B1 * | 8/2001 | Gillies et al. ............... 600/411 |
| 6,298,259 B1 * | 10/2001 | Kucharczyk et al. ....... 600/411 |
| 6,304,769 B1 * | 10/2001 | Arenson et al. ............ 600/424 |
| 6,401,723 B1 | 6/2002 | Garibaldi et al. |
| 6,827,723 B2 * | 12/2004 | Carson ..................... 606/130 |
| 7,048,716 B1 * | 5/2006 | Kucharczyk et al. .. 604/164.01 |
| 2002/0065529 A1 * | 5/2002 | Laurent et al. ............ 606/151 |
| 2005/0113846 A1 * | 5/2005 | Carson ..................... 606/130 |

* cited by examiner

*Primary Examiner*—Brian Casler
*Assistant Examiner*—Sanjay Cattungal
(74) *Attorney, Agent, or Firm*—Harness, Dickey & Pierce, P.L.C.

(57) ABSTRACT

A method of navigating the distal end of a medical device through an operating region in a subject's body includes displaying an x-ray image of the operating region, including the distal end of the medical device; determining the location of the distal end of the medical device in a reference frame translatable to the displayed x-ray image; and displaying an enhanced indication of the distal end of the medical device on the x-ray image to facilitate the navigation of the distal end of the device in the operating region.

49 Claims, 5 Drawing Sheets

METHOD OF NAVIGATING MEDICAL DEVICES IN THE PRESENCE OF RADIOPAQUE MATERIAL

FIELD OF THE INVENTION

This invention relates to the navigation of medical devices in the presence of radiopaque materials, and in particular to a method of navigating a medical device for the delivery of radiopaque materials.

BACKGROUND OF THE INVENTION

The navigation of the distal end of a medical device through the body, whether by conventional mechanical means or magnetic means, is usually facilitated by x-ray imaging of the operating region. However, when there is radiopaque material in the operating region, it is often difficult to discern the distal end of the medical device. This occurs, for example when the medical device is delivering a radiopaque material, such as a radiopaque embolic material, or a radiopaque embolization coil. The presence of these materials in the medical device or in the operating region can make it difficult for the physician to "see" the distal end of the medical device on x-ray images, and thus make it difficult to quickly and accurately navigate the distal end of the medical device.

SUMMARY OF THE INVENTION

Broadly, the method of this invention relates the to navigation of medical devices in a subject's body. The method broadly comprises displaying an x-ray image of the operating region, including the distal end of the medical device; determining the location of the distal end of the medical device in a reference frame translatable to the displayed x-ray image; and displaying an enhanced indication of the distal end of the medical device on the x-ray image to facilitate the navigation of the distal end of the device in the operating region. The method of this invention allows a physician to more accurately track the position of the distal end of the medical device during navigation, this facilitates navigation, and particularly the accurate delivery of radiopaque materials in a subject's body.

DETAILED DESCRIPTION OF THE INVENTION

Figure 1:
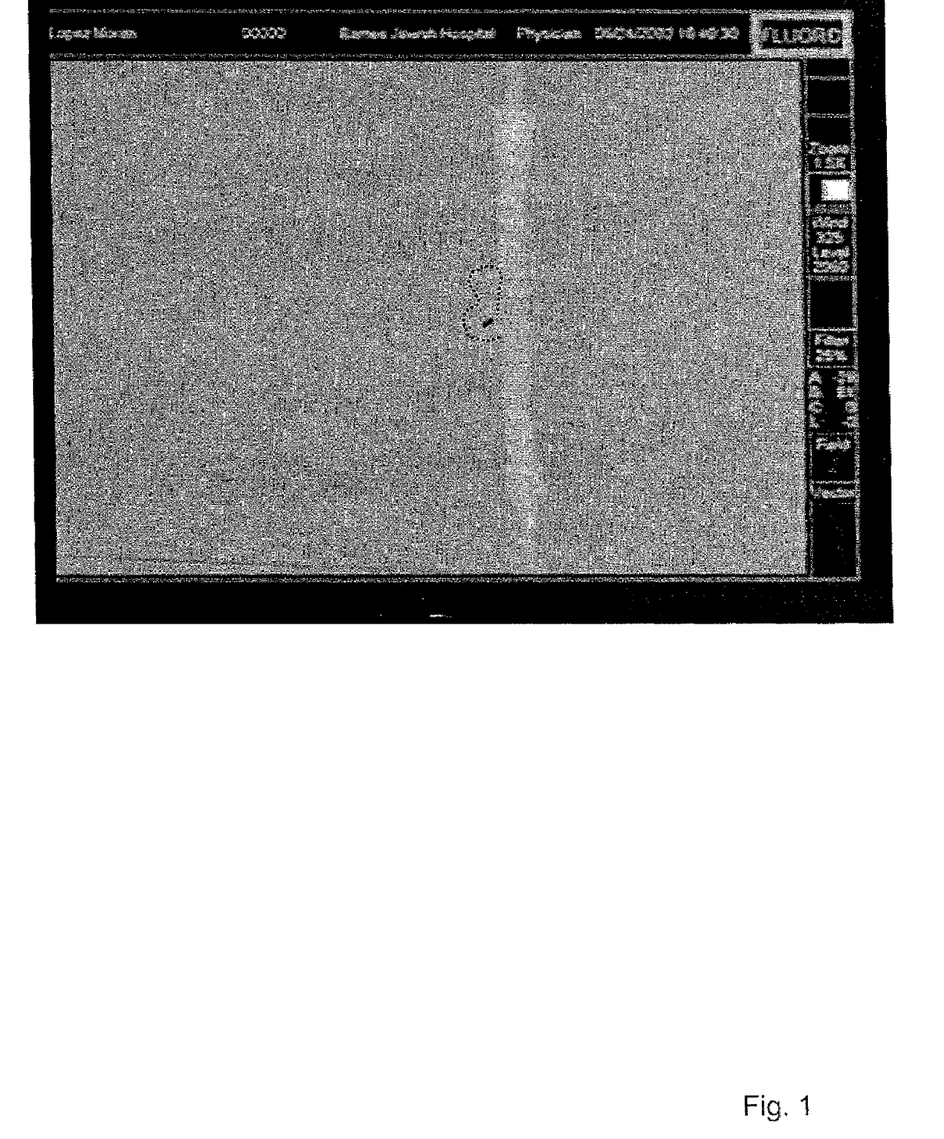
FIG. 1 is a radiograph an aneurysm phantom showing a medical device navigated to the mouth of the aneurysm.
Figure 2A:
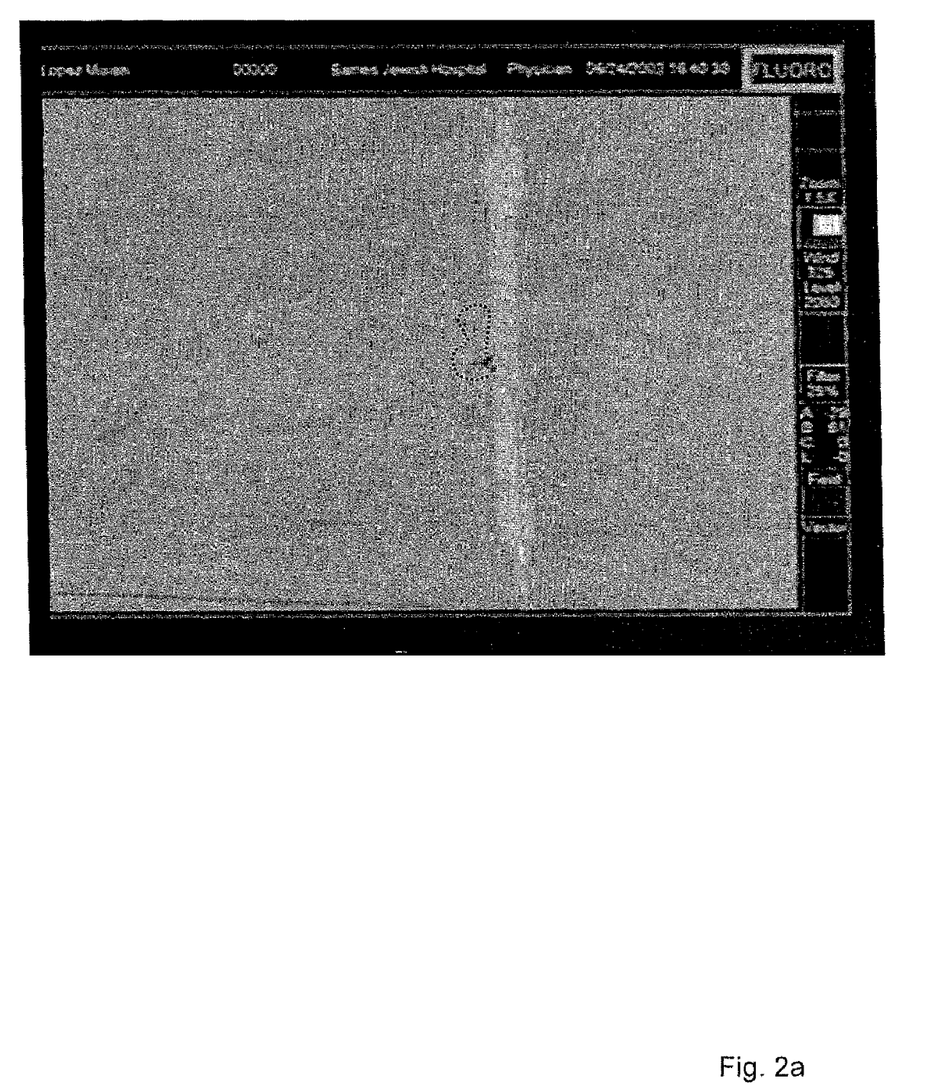
FIG. 2a is a radiograph of an aneurysm phantom and catheter after radiopaque coils have been released into the aneurysm body.
Figure 2B:
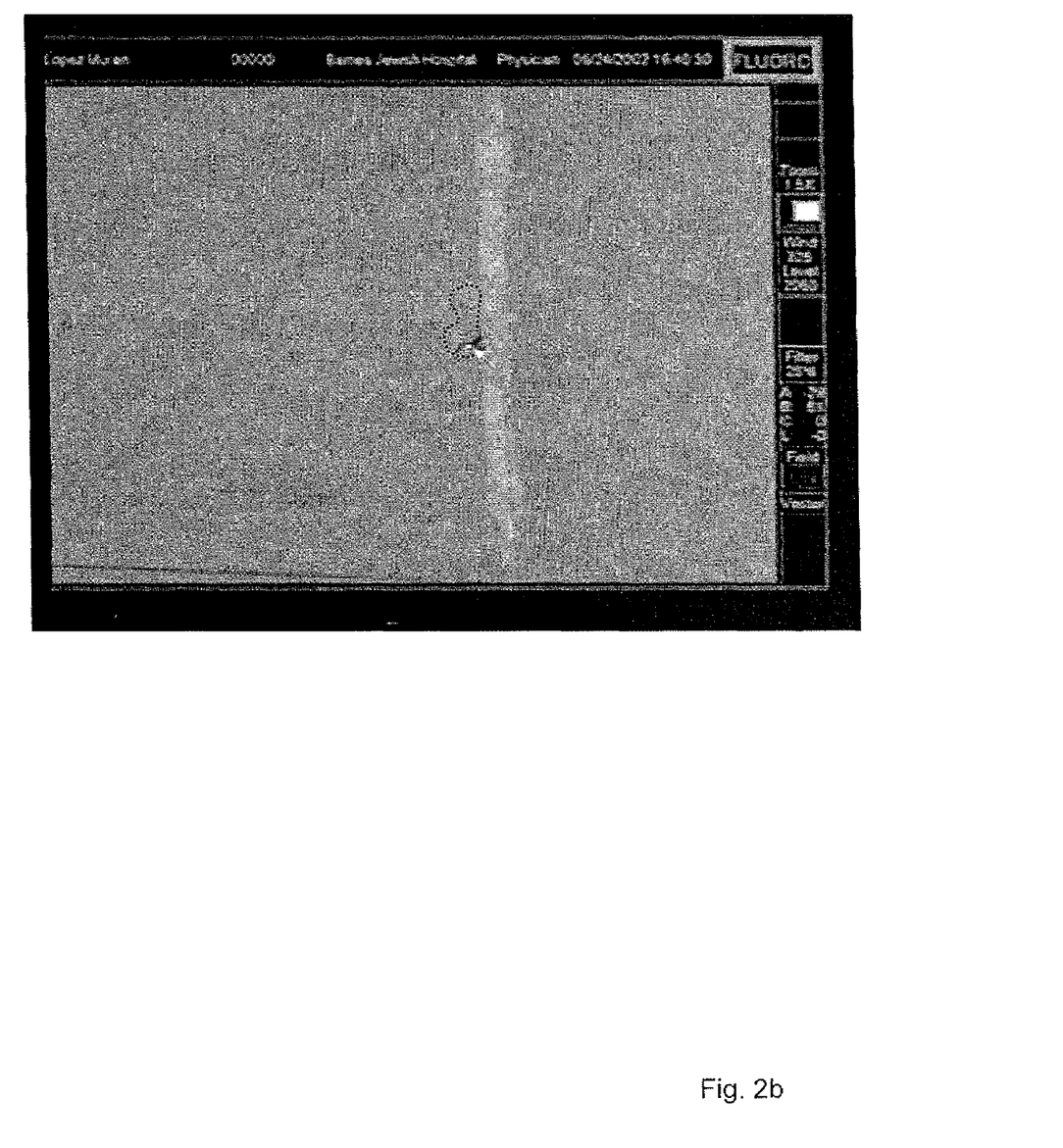
FIG. 2b is a radiograph show in FIG. 2a with an line indicating the distal end of the medical device and an arrow indicating the distal end of the medical device, in accordance with the principles of this invention.

The present invention relates to a method of navigating the distal end of a medical device through an operating region in a subject's body. Broadly, this method comprises displaying an x-ray or other image of the operating region, including the distal end of the medical device, for example as shown in FIG. 1. The location of the distal end of the medical device is then determined in a reference frame translatable to the displayed x-ray image. Based upon the determined location, an enhanced indication of the distal end of the medical device is then displayed on the x-ray image to facilitate the navigation of the distal end of the device in the operating region. This is shown in FIG. 2. This helps the user identify the location of the distal end of the medical device, to facilitate navigating the device.

This method can be used with any type of medical device, such as a catheter, endoscope, guide wire, sampling (e.g. biopsy) device, drug or device delivery catheter, sensing device, or pacing device, etc. The method can be employed with conventional navigation, i.e. devices with preformed tips for manipulation in the body, or devices with pull or push wires for directing the distal tip of the medical device. The method can also be employed with non-conventional navigation modes such as magnetic navigation, (e.g. the application of an external magnetic field to orient the distal tip) or the use of magnetostrictive or electrostrictive devices to direct the distal tip of the medical device.

While described herein in terms of x-ray imaging and interference from radio opaque materials, this invention also applies to other imaging modalities where there is material present which interferes with the accurate imaging and display of the distal end of the medical device. In such cases, the distal tip can still be localized, and the position indicated independent of the local interference.

Figure 3:
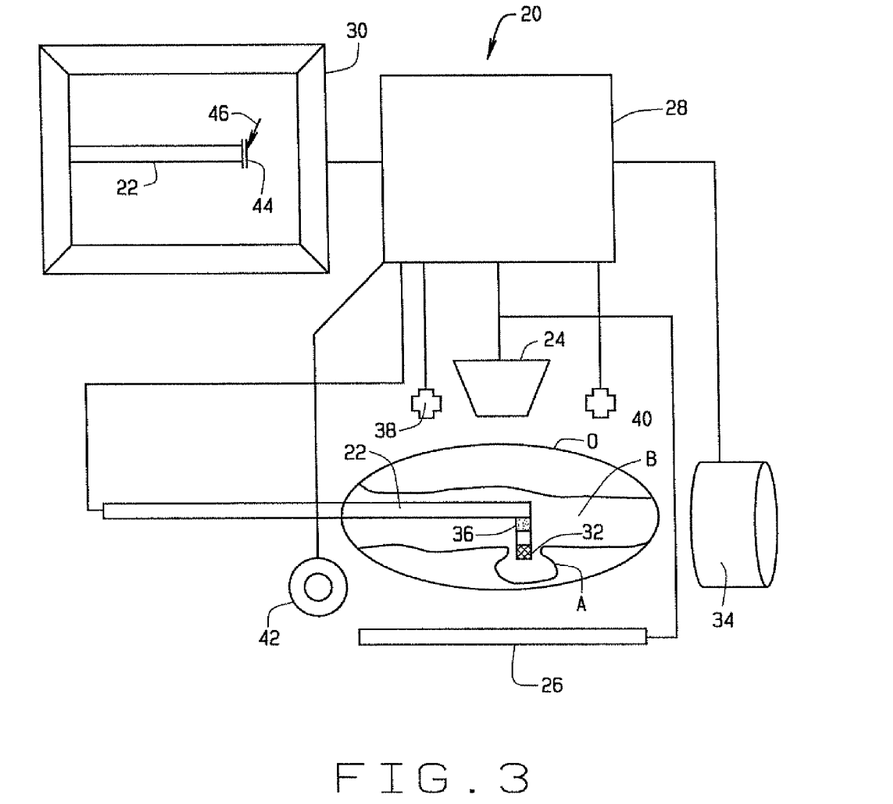
FIG. 3 is a schematic diagram of a system for carrying out the method of the present invention.

As shown schematically in FIG. 3 a system for implementing the method of this invention is indicated generally as 20. The system 20 comprises a catheter 22 for example, for delivering radio opaque coils to a vascular defect such as an aneurysm A in blood vessel B in the operating region O of the subject. In this preferred embodiment, there is an imaging system comprising an x-ray source 24 and a solid state imaging plate 26 connected through a processor 28 to a display 30. The catheter 22 has a magnetically responsive element 32 so that the distal end of the catheter 22 can be controlled by a external magnet system represented schematically at 34. The embolic substance or embolizing coils used to fill the aneurysm A are typically radiopaque so that they can be seen in x-ray imaging. However, this radiopacity can make it hard to distinguish the distal end of the catheter 22. As shown in FIG. 3, the catheter 22 can include a coil 36 for receiving signals from transmitters 38 and 40 at known fixed locations, in order to determine the position and orientation of the distal end of the catheter 22 in which the coil 36 is located. (Alternatively, the coil 36 could be used as a transmitter, and receivers could be provided in known fixed locations). Based upon these transmitted signals a processor can determine the position and orientation of the distal and of the catheter, and translate this determined position into the frame of reference of the imaging system. The position of the distal end of the catheter 22 could also be determined by displacing the distal end of the catheter and determining the position through image processing. The magnet system 34 could be operated to displace the distal end of the catheter. Alternatively, an auxiliary coil 42 could be used to change the magnetic field applied to the distal end of the catheter to displace the catheter. The coil 36 could be energized to change the magnetic moment of the catheter 22 and cause it to move in the applied magnetic field. Once the position of the distal end of the catheter 22 is determined, the processor 28 can display an enhanced indication of the location of the distal end on the display 30. This enhanced indication may be a line indicating the end, such as double lines 44 or a ring corresponding to the distal end which also would help indicate the orientation, or an pointer, such as arrow 46. The enhanced indication can be of increased brightness, distinctive color or it may flash or alternate or change color.

The step of determining the location of the distal end of the medical device can be accomplished in a number of ways, including transmitting signals between at least one reference location and the distal end of the medical device, and more preferably a plurality of reference locations and the distal end of the medical device.

The distal end of the medical device is preferably provided with a receiver having lead wires that extend to the proximal end of the device, where they are connected to the processor that can process the signals received from transmitters at the reference locations can determine the location of the distal tip in the frame of reference of the reference locations. The position of the distal tip can then be transferred to the frame of reference of the imaging system, and an indication of the location of the tip can displayed on x-ray image. This indication can be a highlighted outline of the distal end, a ring or circle to represent the end, an arrow, or some other indication that gives the user a more accurate view of the current position of the distal tip. For example, the contrast on the X-ray image can change from white to black to make the tip of the catheter blink to indicate its position. A positive indication of the tip position is particularly helpful when the medical device contains radiopaque material for delivering into the body. The radiopaque material can obscure the distal end of the device on x-ray images, impairing navigation.

Figure 4:
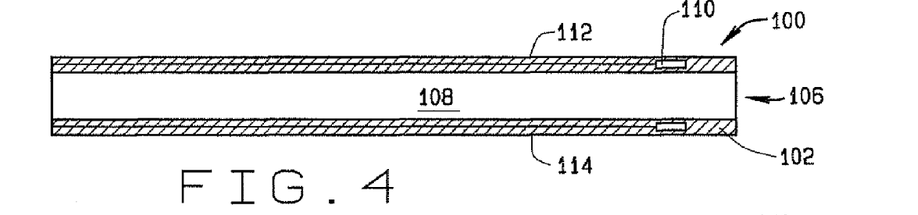
FIG. 4 is a longitudinal cross-sectional view of a catheter incorporating a localization coil in accordance with the principles of this invention.
Figure 5:
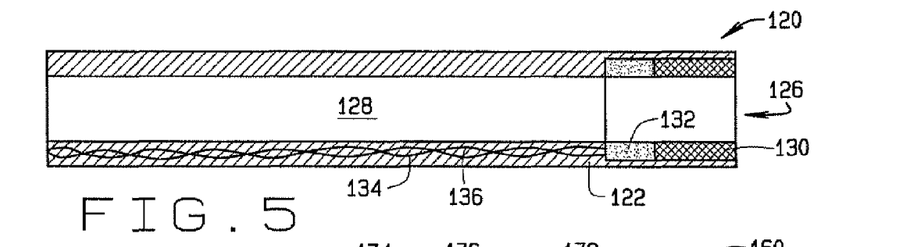
FIG. 5 is a longitudinal cross-sectional view of a magnetically navigable catheter with a localization coil useful in the method of the present invention.

Examples of a conventional catheter and a magnetically navigable catheter adapted for this method are shown in FIGS. 4 and 5. As shown in FIG. 4, a conventional catheter 100 comprises a generally tubular sidewall 102, with a proximal end (not shown), a distal end 106, and a lumen 108 extending therebetween, also has at least one coil 110 adjacent the distal end 106, connected by leads 112 and 114 which extend to the proximal end of the catheter 100. The coil 110 is preferably embedded in the sidewall 102, although it could be secured on the inside or outside of the wall. As shown in FIG. 4, the coil 110 may extend circumferentially around the catheter. Instead of, or in addition to, a circumferentially extending coil, the catheter 100 could have one or more coils in or on the sidewall 102 generally in planes parallel to the axis of the catheter. In some instances it may be preferable to have three mutually perpendicular coils. The coil(s) 110 is preferably made of a radio opaque material (or with other imaging modalities a material that is imaged by such imaging modality so that the distal tip is viewable in the displayed image without the need for a separate marker. Gold and Platinum and alloys of gold or platinum are suitable for this purpose. Alternatively, a radio opaque (or other imagable) marker is provided.

In addition to being used in magnetic localization, the coil(s) 110 can also be used to change the magnetic moment of the distal end of the device to facilitate magnetic navigation of the distal end of the device in a magnetic field applied by an external magnet system, as disclosed in Garibaldi et al., U.S. Pat. No. 6,401,723, issued Jun. 11, 2002, incorporated herein by reference.

As shown in FIG. 5, a magnetically navigable catheter 120 comprises a generally tubular sidewall 122, with a proximal end (not shown), a distal end 126, and a lumen 128 extending therebetween. A tubular magnetically responsive member 130 is embedded in the distal end of the sidewall 122. The magnetically responsive member is preferably made of a permanent magnetic material, such as neodymium-iron-boron or a permeable magnetic material, such as Hiperco, that is of sufficient size and shape to align with an applied magnetic field from an external source magnet (typically about 0.07 to about 0.1T). At least one coil 132 adjacent the distal end 126, is connected by leads 134 and 136 which extend to the proximal end of the catheter. The coil 132 is preferably embedded in the sidewall 122, proximal to the magnetically responsive element although it could be secured on the inside or outside of the wall. As shown in FIG. 5, the coil 132 may extend circumferentially around the catheter. Instead of, or in addition to, a circumferentially extending coil, the catheter 120 could have one or more coils in or on the sidewall generally in planes parallel to the axis of the catheter. In some instances it may be preferable to have three mutually perpendicular coils. The coil(s) 132 is preferably made of a radio opaque material (or with other imaging modalities a material that is imaged by such imaging modality so that the distal tip is viewable in the displayed image without the need for a separate marker. Gold and Platinum and alloys of gold or platinum are suitable for this purpose. Alternatively, a radio opaque (or other imagable) marker is provided.

In addition to being used in magnetic localization, the coil(s) 132 can also be used to change the magnetic moment of the distal end of the device to facilitate magnetic navigation of the distal end of the device in a magnetic field applied by an external magnet system, as disclosed in Garibaldi et al., U.S. Pat. No. 6,401,723, issued Jun. 11, 2002, incorporated herein by reference.

The coil(s) 110 in the catheter 100, and the coil(s) 132 in the catheter 120, and can act as receivers from signals transmitted from transmitters at fixed reference points, or as transmitters of signals to receivers at the fixed reference points.

In a preferred embodiment of the invention, low frequency magnetic fields are generated in a plurality of coils placed around the patient, as originally proposed by Van Steenwyk, et al in U.S. Pat. No. 4,173,228, and further developed by Acker, et al in U.S. Pat. No. 5,558,091 and others (the disclosures of which are incorporated by reference). The coils are capable of generating magnetic fields of about 1 Gauss or $10^{-4}$ Tesla at the location of the catheter tip, and are typically operated at a plurality of frequencies in the one to ten kilo-Hertz range. Sensing of the a.c. magnetic field is simply a matter of measuring the voltage induced by the changing applied magnetic field in a small coil near the catheter distal tip. Signals from the individual external coils occur at distinct frequencies and/or at distinct times, and mathematical triangulation-type algorithms are then used to locate the tip relative to the frame of reference of the external coil set. Measured voltages on the order of one milli-Volt are adequate to locate the tip to within a fraction of one millimeter. The voltage induced in the sense coil is given by:

$$V = -\partial\Phi/\partial t = -NA\partial B/\partial t = -2\pi f B\, NA \quad (1)$$

where
V=voltage induced in the sense coil in volts
f=frequency of applied magnetic field in Hertz
B=amplitude of applied magnetic field in Tesla
NA=turns area product in square m.

For a simple, one layer coil, the turns area product is simply the number of turns in the coil times its cross sectional area. For a multi-layer coil, each layer has its own cross-sectional area, and integrating from the inside to the outside diameter of the coil gives:

$$NA = N_t \pi (d_1^2 + d_1 d_2 + d_2^2)/12 \quad (2)$$

Where
$N_t$=total number of turns in the coil
$d_1$=coil inside diameter
$d_2$=coil outside diameter A worst-case estimate for the total number of turns in the coil assumes that the windings stack on top of one another, and is given by:

$$N_t = L(d_2 - d_1)/(2\, d_w^2) \quad (3)$$

where
L=coil length
$d_w$=wire diameter

Microcatheters which have been developed for drug infusion and repair of vascular defects in the neuro-vasculature are typically less than one mm in outside diameter to facilitate navigation through small blood vessels. These microcatheters have inside diameters up to one-half mm to facilitate optimum delivery volume. Preferred dimensions for a microcatheter embodiment of the present invention are:

$d_1$=0.54 mm $d_2$=0.92 mm

The length of the coil must be rigid, and forms part of a rigid distal tip. The rigid section of the tip would preferably not be larger than about four mm to facilitate passage into vessel side branches. A preferred embodiment has a magnet at the very distal tip of the microcatheter which is about two mm long. Thus, the worst case coil length is two mm. A small but practical gauge of insulated wire for the coil is AWG#55, having an overall diameter of $d_w$=0.018 mm. Inserting these dimensions into Eq.(3), and then into Eq.(2) gives:

$N_t$~1,200.

NA~500 mm$^2$=5×10$^{-4}$ m$^2$ and evaluating Eq.(1) with a typical frequency of f~4×10$^3$ Hz, and B~10$^{-4}$ Tesla gives a signal voltage amplitude estimate of:

V~10$^{-3}$ Volts=1 milli-Volt, which again is ample signal to locate the catheter tip to within a fraction of one mm.

The receive coil(s) at the tip of the catheter contains a total length of wire equal to the average circumference of the coil times the number of turns, and is equal to nine feet in the preferred embodiment above. If AWG #55 copper wire is used to wind this coil, the resistance will be about 300 Ohms. Gold is much more biocompatible than copper, and is preferred. A gold coil will have a resistance of about 420 Ohms in the preferred embodiment. While the higher resistance will generate more thermal noise for a given input signal, the noise scales as the square root of the resistance and is only about 20% higher for gold than for copper. Gold has another very important advantage over copper. The gold coil is radiopaque, and will mark the position of the coil when X-ray guidance is employed. Without this feature, a gold or platinum marker would be required at the catheter tip, which would further lengthen the stiff part of the tip. The combination radiopaque and location sensing coil enables a visual check on the accuracy of the electromagnetic localization when the coil is visible under fluoroscopy, because an accurate electromagnetic location mark should fall on top of the radiopaque tip when displayed on the X-ray monitor. Conventional guidance using X-ray fluoroscopy can be employed until the tip becomes obscured by other radiopaque materials, after which electromagnetic localization can be employed. In short, there are advantages to having a bi-modal localization capability in the tip coil. While platinum is a more conventional radiopaque marker material, a platinum coil in the preferred embodiment would have a resistance of about 1,900 Ohms, and would generate about 250% more thermal noise than the copper coil for a given input signal. Thus, a gold coil is preferred material.

Of course, the distal end of the medical device could be provided with a transmitter, that transmits to receivers at the reference locations, or multiple transmitters or multiple receivers can be provided on the medical device.

In the case of a radio opaque transmitter or receiver on the medical device, the enhanced indication of the distal tip may be an indication of the location of this coil, thus the user "sees" the coil on images, and where there is interference the method of the invention provides an enhanced display of the location of the coil, so the user has the same reference point, regardless of whether the coil can actually be seen in the image.

Other methods of localizing the distal end of the medical device can be used, such as ultrasound or electric-potential.

The step of determining the location of the distal end of the medical device can also be accomplished by displacing the distal end of the device slightly, and through processing the images before and after the displacement determining the position of the distal end of the medical device. This allows the position of the distal end to be determined in the frame of reference of the x-ray image, so that the position of the distal tip of the medical device can be readily indicated on the display. In the case of a conventionally navigated medical device, the displacement can be by rotating the proximal end, by advancing an/or retracting the proximal end, or by manipulating the tip with push wires or pull wires. In the case of non-conventionally navigated device, the distal tip can be displaced by operating an electrostrictive or magnetostrictive element.

Figure 6:
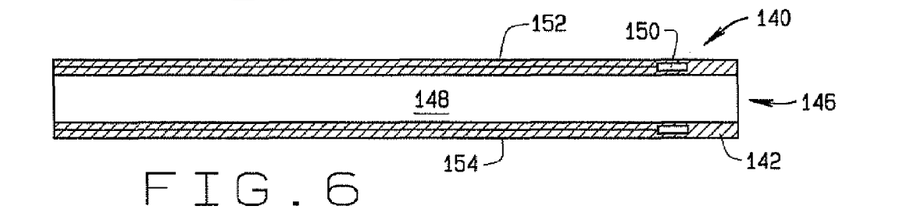
FIG. 6 is a longitudinal cross-sectional view of a catheter incorporating a displacement coil useful in the method of the present invention.
Figure 7:
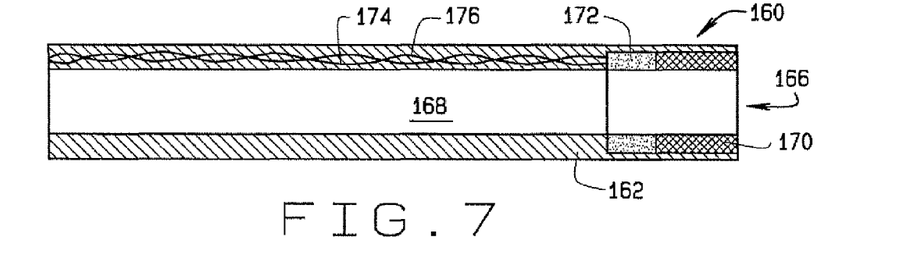
FIG. 7 is a longitudinal cross-sectional view of a magnetically navigable catheter with a displacement coil useful in the method of the present invention.

Examples of a conventional catheter and a magnetically navigable catheter adapted for this method are shown in FIGS. 6 and 7. As shown in FIG. 6, a conventional catheter 140 comprises a generally tubular sidewall 142, with a proximal end (not shown), a distal end 146, and a lumen 148 extending therebetween, also has at least one coil 150 adjacent the distal end 146, connected by leads 152 and 154 which extend to the proximal end of the catheter. The coil 150 is preferably embedded in the sidewall 62, although it could be secured on the inside or outside of the wall. As shown in FIG. 6, the coil 150 may extend circumferentially around the catheter 140. Instead of, or in addition to, a circumferentially extending coil, the catheter 140 could have one or more coils in or on the sidewall generally in planes parallel to the axis of the catheter. In some instances it may be preferable to have three mutually perpendicular coils. The coil 150 is preferably made of a radio opaque material (or with other imaging modalities a material that is imaged by such imaging modality so that the distal tip is viewable in the displayed image without the need for a separate marker. Gold and Platinum and alloys of gold or platinum are suitable for this purpose. Alternatively, a radio opaque (or other imagable) marker is provided.

In addition to being used in displacing the distal end of the catheter 140, the coil(s) 150 can also be used to change the magnetic moment of the distal end of the device to facilitate magnetic navigation of the distal end of the device in a magnetic field applied by an external magnet system, as disclosed in Garibaldi et al., U.S. Pat. No. 6,401,723, issued Jun. 11, 2002, incorporated herein by reference.

As shown in FIG. 7, a magnetically navigable catheter 160 comprises a generally tubular sidewall 162, with a proximal end (not shown), a distal end 166, and a lumen 168 extending therebetween. A tubular magnetically responsive member 170 is embedded in the distal end of the sidewall 162. The magnetically responsive member is preferably made of a permanent magnetic material, such as neodymium-iron-boron or a permeable magnetic material, such as Hiperco, that is of sufficient size and shape to align with an applied magnetic field from an external source magnet. At least one coil 172 adjacent the distal end 166, connected by leads 174 and 176 which extend to the proximal end of the catheter. The coil 172 is preferably embedded in the sidewall 162, proximal to the magnet although it could be secured on the inside or outside of the wall. As shown in FIG. 7, the coil 172 may extend circumferentially around the catheter 160. Instead of, or in addition to, a circumferentially extending coil, the catheter 160 could have one or more coils in or on the sidewall generally in planes parallel to the axis of the catheter. In some instances it may be preferable to have three mutually perpendicular coils.

The coil 172 is preferably made of a radio opaque material (or with other imaging modalities a material that is imaged by such imaging modality so that the distal tip is viewable in the displayed image without the need for a separate marker. Gold and Platinum and alloys of gold or platinum are suitable for this purpose. Alternatively, a radio opaque (or other imagable) marker is provided.

In addition to being used in displacing the distal end of the catheter 160, the coil(s) 172 can also be used to change the magnetic moment of the distal end of the device to facilitate magnetic navigation of the distal end of the device in a magnetic field applied by an external magnet system, as disclosed in Garibaldi et al., U.S. Pat. No. 6,401,723, issued Jun. 11, 2002, incorporated herein by reference.

The coil(s) 150 in the catheter 140, and the coil(s) 172 in the catheter 160, and can be selectively connected to a source of electric power to change the magnetic moment of the distal end of the catheter, thereby temporarily displacing the distal end of the catheter so that the location of the distal end of the catheter can be located by signal processing.

In the case of a magnetically navigated medical device, in which the medical device has a magnetically responsive element for aligning with an applied magnetic field the displacement of the distal tip can be effected by changing the direction or intensity of the applied magnetic fields from the external source magnet. An auxiliary magnet can also be provided outside the body to change the position of the distal end of the medical device. This auxiliary magnet could be a permanent magnet, but is preferably an electromagnet so that the field can be turned on and off. An auxiliary coil could alternatively be provided on the medical device, to temporarily change the magnetic moment of the medical device to displace the medical device within the magnetic field of the external source magnets.

Figure 8:
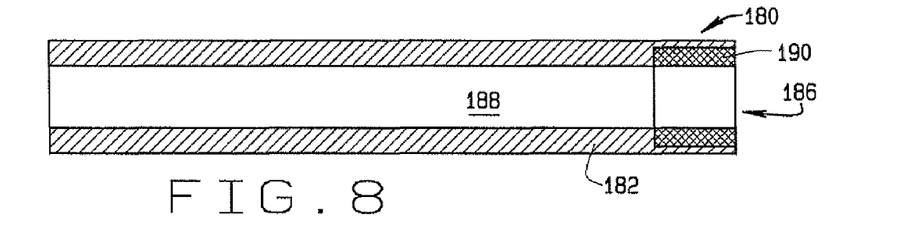
FIG. 8 is a longitudinal cross-sectional view of a magnetically navigable catheter useful in the method of the present invention.

As shown in FIG. 8, a magnetically navigable catheter 180 comprises a generally tubular sidewall 182, with a proximal end (not shown), a distal end 186, and a lumen 188 extending therebetween. A tubular magnetically responsive member 190 is embedded in the distal end of the sidewall 182. The magnetically responsive member is preferably made of a permanent magnetic material, such as neodymium-iron-boron or a permeable magnetic material, such as Hiperco, that is of sufficient size and shape to align with an applied magnetic field from an external source magnet. The distal tip of catheter 80 responds to changes in the applied magnetic field and can be displaced by changing the magnetic field being applied by the external source magnet, or by temporarily using an auxiliary or boost magnet to displace the distal tip. A radio opaque marker could be provided to facilitate viewing the distal tip on x-ray images.

The method of the present invention is particularly useful for navigating medical devices that deliver radiopaque materials, such as flowable, settable embolic materials, or embolizing coils. In these cases the radiopaque material inside the medical device can make it difficult to accurately locate the distal end of the device in an x-ray image. It can be even more difficult after radiopaque material has been ejected from the medical device into the operating region. Thus, for example, in navigating the distal end of a catheter to the site of a vascular defect, such as an aneurysm, the user may not be able to accurately identify the distal end of the catheter, impairing navigation. Once radiopaque material (e.g., a flowable, settable embolic material or embolizing coils) has been ejected from the catheter, it can even more difficult to identify the distal end of the catheter to complete the procedure. The present invention solves this difficulty by accurately locating the tip, and indicating the position of the tip on the displayed x-ray image of the operating region. The user can then determine how best to position the distal tip to complete the procedures.

What is claimed is:

1. A method of navigating the distal end of a medical device through an operating region in a subject's body, the method comprising:

introducing the distal end of an elongate medical device having at least one magnetically responsive element fixed thereon into the subiect's body;

navigating the distal end of the medical device to the desired site of delivery;

expelling a flowable radiopague substance from the medical device at the desired site of delivery;

displaying an X-ray image of the operating region, including the distal end of the medical device;

determining the location of a localization coil in the distal end of the medical device relative to at least two transmitters at known reference locations, to establish a distal end location in a reference frame translatable to the displayed image; and displaying an enhanced indication of the distal end of the medical device on the X-ray image of the operating region in which the distal end of the medical device is in the presence of the expelled flowable radiopague substance, to facilitate the navigation of the distal end of the device in the operating region.

2. The method according to claim 1, wherein the step of determining the location of the distal end of the medical device comprises transmitting signals between at least one reference location and the distal end of the medical device.

3. The method according to claim 2 wherein the step of transmitting signals between at least one reference location and the distal end of the device comprises transmitting signals from a plurality of transmitters in more than one reference relocation, and a receiver on the magnetic medical device.

4. The method according to claim 2 wherein the medical device has a transmitter or receiver coil made from a radio opaque material.

5. The method according to claim 4 wherein the coil is made from at least one of gold or platinum, or an alloy containing gold or platinum.

6. The method according to claim 1, wherein the step of determining the location of the distal end of the medical device comprises moving the distal end of the medical device, and processing x-ray images before and after the movement to determine the location of the distal tip.

7. The method according to claim 6, wherein the distal end of the medical device includes a magnetically responsive element, and wherein the step of moving the distal end of the medical device comprises applying a magnetic field or gradient from a magnet outside the subject's body to move the magnetically responsive element and thus the distal end of the medical device.

8. The method according to claim 7 wherein the medical device has a magnetically responsive element, wherein the medical device is oriented by the applying a magnetic field from a magnetic surgery system outside the subject's body, and wherein the step of displacing the distal tip comprises changing the magnetic field applied by the magnetic surgery system to the magnetically responsive element.

9. The method according to claim 1 wherein the medical device includes at least one coil, and wherein the step of displacing the medical device comprises applying a current to the at least one coil to displace the at least one coil, and thus the medical device.

10. A method of navigating the distal end of a medical device through an operating region in a subject's body, in which radiopaque flowable substances in the operating region make it difficult to visualize the distal end of the medical device, the method comprising:

navigating the distal end of an elongate medical device having at least one magnetically responsive element fixed thereon to a desired site of delivery;

displaying an x-ray image of the operating region, including the distal end of the medical device having a radiopaque substance therein;

expelling a flowable radiopague substances from the end of the medical device into the operating region;

determining the location of a localization coil in the distal end of the medical device relative to at least two transmitters at known reference locations, to establish a distal end location in a reference frame translatable to the displayed x-ray image; and displaying an enhanced indication of the distal end of the medical device on the x-ray image of the operating region in which the distal end of the medical device is in the presence of the expelled flowable radiopague substance, based on the determined location of the distal end relative to at least one reference location in the reference frame, to provide a positive visible indication of the distal end when the distal end may be difficult to see in the x-ray image, to facilitate the navigation of the distal end of the device in the operating region.

11. The method according to claim 10 wherein the radiopaque objects in the operating region include objects that have been expelled from the magnetic medical device and/or objects in the medical device.

12. The method according to claim 11 wherein the radiopaque objects in the operating region include objects that have been expelled from the magnetic medical device.

13. The method according to claim 11 wherein the radiopaque objects in the operating region include objects in the medical device.

14. The method according to claim 11, wherein the step of determining the location of the distal end of the medical device comprises transmitting signals between at least one reference location and the distal end of the medical device.

15. The method according to claim 12 wherein the step of transmitting signals between at least one reference location and the distal end of the device comprises transmitting signals from a plurality of transmitters in more than one reference relocation, and a receiver on the magnetic medical device.

16. The method according to claim 14 wherein the medical device has a transmitter or receiver coil made from a radio opaque material.

17. The method according to claim 16 wherein the coil is made from at least one of gold or platinum, or an alloy containing gold or platinum.

18. The method according to claim 10, further comprising the step of determining the location of the distal end of the medical device comprises moving the distal end of the medical device, and processing x-ray images before and after the movement to determine the location of the distal tip.

19. The method according to claim 18, wherein the distal end of the medical device includes a magnetically responsive element, and wherein the step of moving the distal end of the medical device comprises applying a magnetic field or gradient from a magnet outside the subject's body to move the magnetically responsive element and thus the distal end of the medical device.

20. The method according to claim 19 wherein the medical device has a magnetically responsive element, wherein the medical device is oriented by applying a magnetic field from a magnetic surgery system outside the subject's body, and wherein the step of displacing the distal tip comprises changing the magnetic field applied by the magnetic surgery system to the magnetically responsive element.

21. The method according to claim 11 wherein the medical device includes at least one coil, and wherein the step of displacing the medical device comprises applying a current to the at least one coil to displace the at least one coil, and thus the medical device.

22. The method according to claim 21 wherein the coil is also used to change the magnetic moment of the distal end of the device to orient the distal end of the device.

23. The method according to claim 11 wherein the medical device is adapted to deliver embolizing devices from its distal end to embolize a vascular defect, and further comprising the step of positioning the distal end of the medical device in the vascular defect, and ejecting an embolizing device from the distal end to embolize the vascular defect.

24. The method according to claim 11 wherein the medical device is adapted to deliver embolizing material from its distal end to embolize a vascular defect, and further comprising the step of positioning the distal end of the medical device in the vascular defect, and ejecting an embolizing material from the distal end to embolize the vascular defect.

25. A method of delivering a flowable radiopaque substance to an operating region in a subject's body, the method comprising:
   introducing the distal end of an elongate medical device into the subject's body which medical device includes at least one magnetically responsive element fixed thereon and a localization coil made of a radiopague material so as to be visible in the X-ray image;
   navigating the distal end of the medical device to the desired site of delivery;
   expelling a flowable radiopague substance at the desired site of delivery
   displaying an x-ray image of the operating region, including the distal end of the medical device;
   determining the location of a localization coil in the distal end of the medical device relative to at least two transmitters at known reference locations, to establish the location of the distal end being navigated in the presence of a radiopaque substance, in a reference frame translatable to the displayed x-ray image;
   displaying an enhanced indication of the distal end of the medical device on the x-ray image of the operating region in which the distal end of the medical device including a radiopague material is in the presence of the expelled flowable radiopague substance, to facilitate the navigation of the distal end of the device in the operating region; and
   navigating the distal end of the device using the displayed enhanced indication of the distal end when the distal end is obscured by the radiopaque substance.

26. The method according to claim 25 wherein the radiopaque substance is a flowable, settable embolic material.

27. The method according to claim 25 wherein the radiopaque substance is at least one embolizing coil.

28. The method according to claim 25 wherein the distal end of the magnetic medical device includes a magnetically responsive element, and wherein the step of navigating the distal end of the device includes applying a magnetic field from an external source to orient the distal end of the medical device.

29. The method according to claim 25, wherein the step of determining the location of the distal end of the medical device comprises transmitting signals between at least one reference location and the distal end of the medical device.

30. The method according to claim 25 wherein the step of transmitting signals between at least one reference location and the distal end of the device comprises transmitting signals from a plurality of transmitters in more than one reference relocation, and a receiver on the magnetic medical device.

31. The method according to claim 25, wherein the third step of determining the location of the distal end of the medical device comprises the moving the distal end of the medical device, and processing x-ray images before and after the movement to determine the location of the distal tip.

32. The method according to claim 31, wherein the distal end of the medical device includes a magnetically responsive element, and wherein the step of moving the distal end of the medical device comprises applying a magnetic field or gradient from a magnet outside the subject's body to move the magnetically responsive element and thus the distal end of the medical device.

33. The method according to claim 32 wherein the medical device has a magnetically responsive element, wherein the medical device is oriented by applying a magnetic field from a magnetic surgery system outside the subject's body, and wherein the step of displacing the distal tip comprises changing the magnetic field applied by the magnetic surgery system to the magnetically responsive element.

34. The method according to claim 25 wherein the medical device includes at least one coil, and wherein the step of displacing the medical device comprises applying a current to the at least one coil to displace the at least one coil, and thus the medical device.

35. A method of embolizing a vascular defect in an operating region in a subject's body, comprising:
   introducing the distal end of an elongate medical device having at least one magnetically responsive element fixed thereon into the subject's body;
   navigating the distal end of the device to the vascular defect;
   expelling the flowable radiopague substance at the site of the vascular defect;
   displaying an x-ray image of the operating region, including the distal end of the medical device which includes a localization coil made of a radiopague material so as to be visible in the X-ray image;
   determining the location of a localization coil in the distal end of the medical device relative to at least two transmitters at known reference locations, to establish the location of the distal end being navigated in the presence of a radiopaque substance, in a reference frame translatable to the displayed x-ray image;
   displaying an enhanced indication of the distal end of the medical device on the x-ray image of the operating region in which the distal end of the medical device including a radiopapue material is in the presence of the expelled flowable radiopague substance, to facilitate the navigation of the distal end of the device in the operating region; and
   navigating the distal end of the device using the displayed enhanced indication of the distal end when the distal end is obscured by the radiopaque substance.

36. The method according to claim 35 wherein distal end of the magnetic medical device includes a magnetically responsive element, and wherein the step of navigating the distal end of the device includes applying a magnetic field from an external source to orient the distal end of the medical device.

37. The method according to claim 35 wherein the vascular defect is an aneurysm.

38. The method according to claim 35, wherein the step of determining the location of the distal end of the medical device comprises transmitting signals between at least one reference location and the distal end of the medical device.

39. The method according to claim 38 wherein the medical device has a transmitter or receiver coil made from a radio opaque material.

40. The method according to claim 39 wherein the coil is made from at least one of gold or platinum, or an alloy containing gold or platinum.

41. The method according to claim 40 wherein the step of transmitting signals between at least one reference location and the distal end of the device comprises transmitting signals from a plurality of transmitters in more than one reference relocation, and a receiver on the magnetic medical device.

42. The method according to claim 35, wherein the step of determining the location of the distal end of the medical device comprises moving the distal end of the medical device, and processing x-ray images before and after the movement to determine the location of the distal tip.

43. The method according to claim 42, wherein the distal end of the medical device includes a magnetically responsive element, and wherein the step of moving the distal end of the medical device comprises applying a magnetic field or gradient from a magnet outside the subject's body to move the magnetically responsive element and thus the distal end of the medical device.

44. The method according to claim 43 wherein the medical device has a magnetically responsive element, wherein the medical device is oriented by applying a magnetic field from a magnetic surgery system outside the subject's body, and wherein the step of displacing the distal tip comprises changing the magnetic field applied by the magnetic surgery system to the magnetically responsive element.

45. The method according to claim 35 wherein the medical device includes at least one coil, and wherein the step of displacing the medical device comprises applying a current to the at least one coil to displace the at least one coil, and thus the medical device.

46. The method of claim 35 wherein determining the step of determining the location of a localization coil in the distal end comprises at least two transmitters each having separate known reference relocations generating magnetic fields of about 1 Gauss at frequencies in the one to ten kilo-Hertz range, which are received by a localization coil on the magnetic medical device, such that the location of the coil in the distal end may be determined from the signals received by the coils uisng mathematical triangulation, when the tip is being magnetically navigated in the presence of radiopaque materials that obscure X-ray imaging of the tip location.

47. The method of claim 46 wherein the enhanced indication includes at least one line, which is viewable over the radiopaque material displayed in the X-ray image.

48. The method of claim 47 wherein the enhanced indication including at least one line further includes an increased brightness, distinctive color, or flashing color change.

49. The method of claim 46 wherein the enhanced indication includes a displayed object that can change from white to black in contrast on the X-ray image, to make the tip of the catheter blink to indicate its position when the tip is obscured due to the presence of a flowable radiopaque material.

* * * * *